(12) United States Patent
Chen et al.

(10) Patent No.: US 10,894,037 B2
(45) Date of Patent: Jan. 19, 2021

(54) INHIBITORS OF BACTERIAL TWO COMPONENT SIGNAL TRANSDUCTION SYSTEM AND USES THEREOF

(71) Applicant: Academia Sinica, Taipei (TW)

(72) Inventors: Chinpan Chen, Taipei (TW); Tien-Sheng Tseng, Taipei (TW); Keng-Chang Tsai, Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 16/233,280

(22) Filed: Dec. 27, 2018

(65) Prior Publication Data

US 2019/0192487 A1   Jun. 27, 2019

Related U.S. Application Data (60) Provisional application No. 62/610,534, filed on Dec. 27, 2017.

(51) Int. Cl.
*A61K 31/422* (2006.01)
*A61K 45/06* (2006.01)
*A61K 31/385* (2006.01)

(52) U.S. Cl.
CPC .......... *A61K 31/422* (2013.01); *A61K 31/385* (2013.01); *A61K 45/06* (2013.01)

(58) Field of Classification Search
CPC .............................. A61K 31/422; A61K 45/06
See application file for complete search history.

(56) References Cited

PUBLICATIONS

Lou et al., "Structure and dynamics of polymyxin-resistance-associated response regulator PmrA in complex with promoter DNA", Nature Communications, Nov. 13, 2015.
Garcia-Calderon et al., "Rcs and PhoPQ Regulatory Overlap in the Control of *Salmonella enterica* Virulence", Journal of Bacteriology Sep. 2007, vol. 190, p. 6635-6644.
Chen et al., "The Biology of the PmrA/PmrB Two-Component System: The Major Regulator of Lipopolysaccharide Modifications", Annual review of microbiology, 2013.
Delgado et al., "The PmrA/PmrB and RcsC/YojN/RcsB systems control expression of the*Salmonella* O-antigen chain length determinant", Molecular microbiology, Feb. 21, 2006.
Jo et al., "Improved Oxacillin Treatment Outcomes in Experimental Skin and Lung Infection by a Methicillin-Resistant *Staphylococcus aureus* Isolate with a vraSR Operon Deletion", Antimicrobial agents and chemotherapy, Jun. 2011, p. 2818-2823.
Cheng et al., "Molecular characterization of the PhoPQ-PmrDPmrAB mediated pathway regulating polymyxin B resistance in Klebsiella pneumoniae CG43", Journal of Biomedical Science, 2010.

*Primary Examiner* — Samira J Jean-Louis (57) ABSTRACT

Disclosed herein are novel uses of a compound of formula (I) as an inhibitor of bacterial two component signal transduction system (TCS),

$$A\text{-}L\text{-}B\text{-}L\text{-}A \quad (I)$$

wherein, A is a moiety having a negative charge; L is $-(C_2H_5-O)_n-CH_2-$ or a moiety consists of a carbocyclyl and a heterocyclyl respectively having 5 to 10 ring atoms and coupling together, in which n is 0 or 1; and B is a 5 to 10-membered carbocyclyl or heterocyclyl. The compound of formula (I) may suppress or inhibit the growth of bacteria, including the notorious multi-drug resistant bacteria.

5 Claims, 8 Drawing Sheets

Specification includes a Sequence Listing.

A half-1 half-2
Ch1phar Ch2phar

B

Ch2phar

C

Ch2pharN4

SEQUENCE LISTING

<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Leu Glu His His His His His His
1               5

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
atttcttaat attatcctaa gcaag                                     25

INHIBITORS OF BACTERIAL TWO COMPONENT SIGNAL TRANSDUCTION SYSTEM AND USES THEREOF

CROSS REFERENCE TO RELATED APPLICATION

This application claims priority under 35 U.S.C. § 119(e) to U.S. Provisional Application, U.S. Ser. No. 62/610,534, filed Dec. 27, 2017, which is incorporated by reference herein in its entirety.

BACKGROUND OF THE INVENTION

1. Field of the Invention

The present disclosure relates in general, to the field of anti-bacterials, and to the treatment of disorders caused by bacterial infection.

2. Description of Related Art

Two component signal transduction systems (TCS) are systems that control the expression of genes responsive to the environment and that are composed of sensor proteins exhibiting histidine kinase (HK) activity and regulators which are DNA-binding proteins.

Bacteria have various sensors and regulators for responding to various changes in environment, accordingly, TCS plays important roles in the growth and maintenance and functionality of many different microorganisms, such as regulation of the production of exopolysaccharides and virulence factors, regulation of motility, attachment and biofilm formation; and growth and maintenance of viability. Such TCS bacteria are killed by inhibiting the response regulators of TCS, or inhibitors of TCS. Thus, a promising antimicrobial agent is one having antimicrobial activity against such bacterial TCS system, particularly against response regulators of TCS.

In view of the foregoing, there exists in this art a need of a novel anti-bacteria agent that are inhibitors of TCS, which may suppress the growth of bacteria, particularly, the growth of drug-resistant bacteria.

SUMMARY

The present disclosure is based, at least in part, unexpected discovery that some compounds are effective in disrupting the binding between bacterial response regulator and DNA, thus may suppress the growth of the bacteria, particularly, the multi-drug resistant (MDR) bacteria. Accordingly, these compounds are potential candidates as the lead compounds for the development of a medicament suitable for treating a bacterial infectious disease, such as pneumonia, sepsis, cornea infection, skin infection, an infection in the central neuron system, or a toxic shock syndrome.

Accordingly, it is the first aspect of the present disclosure to provide a method of treating a bacterial infectious disease in a subject, comprising administering to the subject, an effective amount of a compound of formula (I), or a pharmaceutically acceptable salt, hydrate, or solvate thereof,

A-L-B-L-A  (I)

wherein,
A is a moiety having a negative charge;
L is $-(C_2H_5-O)_n CH_2-$ or a moiety consists of a carbocyclyl and a heterocyclyl respectively having 5 to 10 ring atoms and coupling together, in which n is 0 or 1; and
B is a 5 to 10-membered carbocyclyl or heterocyclyl; so as to alleviate or ameliorate the symptoms of the bacterial infectious disease.

According to embodiments of the present disclosure, the compound of formula (I) is an inhibitor of a bacterial PmrA/PmrB system.

According to embodiments of the present disclosure, A is a $-PO_4^-$, $PO_3^{2-}$ or $-SO_3^-$. In a preferred example, A is $-SO_3^-$.

According to one preferred embodiment of the present disclosure, A is $-SO_3^-$; L is and B is $-C_6H_4-$.

According to another preferred embodiment of the present disclosure, A is $-SO_3^-$; L is $-(C_2H_5-O)_n-CH_2-$, in which n is 1; and B is According to still another preferred embodiment of the present disclosure, A is $-SO_3^-$; L is $-(C_2H_5-O)_n-CH_2-$, in which n is 0; and B is According to embodiments of the present disclosure, the bacteria is any of Bacillus anthracis, Bacillus subtilis, Bacillus cereus, Corynebacterium diptheriae, Clostridium tetani, Clostridium botulinum, Clostridium perfringes, Clostridium difficile, Clostridium scindens, Enterococcim Streptococcus viridians, Enterococcus faecalis, Enterococcus foecium, Erysipelothrix rhusiopathiae, Escherichia Coli, Helicobacter pylori, Klebsiella pneumoniae, Listeria monocytogens, Mycobacterium tuberculosis, Propionbacterium acnes, Rhodococcus equi, Staphylococcus agalactiae, Staphylococcus aureus, Staphylococcus epidermidis, Staphylococcus pneumonia, Staphylococcus pyrogens, or Staphylococcus saprophyticus.

According to preferred embodiments, the bacteria is multi-drug resistant bacteria.

According to certain embodiments, the bacteria is polymyxin- or colistin-resistant Klebsiella pneumoniae.

According to certain embodiments, the bacteria is clarithromycin-resistant Helicobacter pylori.

According to other embodiments, the bacteria is rifamycin- or isoniazid-resistant *Mycobacterium tuberculosis*.

According to some embodiments of the present disclosure, the bacterial infectious disease is pneumonia, sepsis, cornea infection, skin infection, an infection in the central neuron system, or a toxic shock syndrome.

According to other embodiments, the subject has skin abscess, furuncle or skin boil.

According to some embodiments of the present disclosure, the method further comprises administering to the subject another therapeutic agent (e.g., an antibiotic) concurrently with, before and/or after administering the compound of formula (I), so as to alleviate or ameliorate the symptoms of the disease.

According to some preferred embodiments, examples of the antibiotic that may be used with the present method include, but are not limited to, acumycin, ampicillin, amoxycillin, amphotericins, antimycins, anglomycin, avermectins, azithromycin, boromycin, carbomycins, carbapenem, ceftazidime, cethromycin, chloramphenicol, chalcomycin, ciprofloxacin, concanamycins, cirramycin, clarithromycin, colistin, cycloxacillin, daptomycin, desmethyl azithromycin, desertomycins, dihydropikromycin, dirithromycin, doxycycline, enramycin, erythromycin, flurithromycin, flumequin gentamycin, isoniazid, juveninicins, kujimycins, lankamycins, lincomycin, litorin, leucomycins, megalomicins, meropenern, methymycin, midecamycins, mycinamicin I, mycinamicin II, mycinamicin III, mycinamicin IV, mycinamicin V, mycinamicin VI, mycinamicin VII, mycinamicin VIII, narbotmycin, neoantimycin, neornethymycin, netilmicin, neutromycin, niddamycins, norfioxacin, oleandomycins, oligomycins, ossamycin, oxacillin, oxolinic acid, penicillin, pikromycin, piperacillin, platenomycins, polymyxins, rapamycins, relomycin, rifamycins, rosaramicin, roxithromycin, virginiamycin, spiramycin, sporeamycin, staphococcomycin, streptomycin, sulfamethoxazole, swalpamycin, telithromycin, teicoplanin, timentin, tobramycin, ticarcillin, trimethoprim, tetracyclin, zlocillin, and/or a combination thereof. In one preferred example, the antibiotic is polymyxin e.g., polymyxin B). In another preferred example, the antibiotic is colistin.

Accordingly, it is the second aspect of the present disclosure to provide a composition that suppresses the growth of a bacteria having two component signal transduction system (TCS), such as PmrA/PmrB system. The composition is therefore useful for treating a bacterial infectious disease. The composition comprises an effective amount of the afore-described compound of formula (I), its pharmaceutically acceptable salt, hydrate or solvate; and a pharmaceutically acceptable excipient.

The compound of formula (I) is present in the composition about 0.1% to 99% by weight, based on the total amount of the composition. In certain embodiments, the compound of formula (I) is present in the composition at least about 1% by weight, based on the total amount of the composition. In other embodiments, the compound of formula (I) is present in the composition at least about 5% by weight, based on the total amount of the composition. In further embodiments, the compound of formula (I) is present in the composition at least about 10% by weight, based on the total amount of the composition. In still further embodiments, the compound of formula (I) is present in the composition at least about 25% by weight, based on the total amount of the composition.

According to some preferred embodiments, the composition further comprises an antibiotic. Examples of the antibiotic that may be used with the present composition include, but are not limited to, acumycin, ampicillin, amoxycillin, amphotericins, antimycins, anglomycin, avermectins, azithromycin, boromycin, carbomycins, carbapenem, ceftazidime, cethromycin, chloramphenicol, chalcomycin, ciprofloxacin, concanamycins, cirramycin, clarithromycin, colistin, cycloxacillin, daptomycin, desmethyl azithromycin, desertomycins, dihydropikrornycin, dirithrornycin, doxycycline, enramycin, erythromycin, flurithromycin, flumequin gentamycin, isoniazid, juvenimicins, kujimycins, lankamycins, lincomycin, leucomycins, megalomicins, meropenem, methymycin, midecamycins, mycinamicin I, mycinamicin II, mycinamicinIII, mycinamicin IV, mycinamicin V, mycinamicin VI, mycinamicin VII, mycinamicin VIII, narbomycin, neoantimycin, neomethymycin, neutromycin, niddamycins, norfioxacin, oleandomycins, oligomycins, ossamycin, oxacillin, oxolinic acid, penicillin, pikromycin, piperacillin, platenomycins, polymyxins, rapamycins, relomycin, rifamycins, rosaramicin, roxithromycin, virginiamycin, spiramycin, sporeamycin, staphococcomycin, streptomycin, sulfamethoxazole, swalpamycin, telithromycin, teicoplanin, timentin, tobramycin, ticarcillin, trimethoprim, tetracyclin, zlocillin, and/or a combination thereof. In one preferred embodiment, the antibiotic is polymyxin (e.g., polymyxin B). In another preferred embodiment, the antibiotic is colistin.

The details of one or more embodiments of the invention are set forth in the accompanying description below. Other features and advantages of the invention will be apparent from the detail descriptions, and from claims.

BRIEF DESCRIPTION OF THE DRAWINGS

The present description will be better understood from the following detailed description read in light of the accompanying drawings, where:

FIG. 1. Pharmacophore-based inhibitor screening and functional examination. (A) Receptor-ligand pharmacophore generation based on PmrA-DNA complex structure (PDB ID: 4S04) and the generated pharmacophore feature clusters, Ch1phar and Ch2phar. (B) The amplified view of Ch2phar. (C) The Ch2pharN4 pharmacophore scaffold contains four negative charged groups (N1-N4). The complimentarily interactive residues (orange sticks) of PmrA toward Ch2pharN4 are labeled. (D) The ligand pharmacophore mapping results of E1-E5. (E) The FP assay result with the additions of E1-E5 (50 μM). (F) Dose-dependent inhibitions of E1-E3 against PmrA-DNA complex formation determined by FP. (In panels A-D, the mesh sphere in red, blue, magenta, green, and dark-gray represent positive-charged, negative-charged, hydrogen-bond donor, hydrogen-bond acceptor, and excluded volume features, respectively. The PmrA are colored in wheat and orange; DNA are colored in white)

FIG. 2. Determinations of binding site and dissociation constant of E1 toward PmrA. The overlapped 2D $^1H$—$^{15}N$ HSQC-TROSY spectra of (A) inactivated PmrA (black) titrated with E1 (green) and (B) activated PmrA (black) with E1 addition (red). (PmrA: E1=1:3 molar ratio; the purebred residues are labeled in black) (C) The perturbed residues of activated PmrA upon E1 binding were mapped onto the structure (cyan). (D) The overlapped 2D $^1H$—$^{15}N$ HSQC-TROSY spectra of $PmrA_C$ titrated with E1. The perturbed residues are labeled in black. (E) The amplified view of panel D. (F) The titration curves of backbone amide resonances of S167, V169, R207, V209, R210, G213, and Y214 were fitted to the equation valid for a 1:1 complex and the $K_D$=126±34.6 μM. (G) The ITC binding isotherm for the interactions of E1 to $PmrA_C$. (H) The BLI data showing the association and dissociation sensorgrams at distinct E1 concentrations for the interaction of $PmrA_C$.

herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "subject" or "patient" refers to an animal including the human species that is treatable with the compound of the present invention. The term "subject" or "patient" intended to refer to both the male and female gender unless one gender is specifically indicated. Accordingly, the term "subject" or "patient" comprises any mammal which may benefit from the treatment method of the present disclosure.

The term "administered", "administering" or "administration" are used interchangeably herein to refer a mode of delivery, including, without limitation, intraveneously, intramuscularly, intraperitoneally, intraarterially, subcutaneously, or transdermally administering an agent (e.g., a compound or a composition) of the present invention.

The term "an effective amount" as used herein refers to an amount effective, at dosages, and for periods of time necessary, to achieve the desired result with respect to the treatment of a disease. For example, in the treatment of an infection, an agent (i.e., a compound or a composition) which decrease, prevents, delays or suppresses or arrests any symptoms of the infection would be effective. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two or more doses in a suitable form to be administered at one, two or more times throughout a designated time period.

The term "a sufficient amount" as used herein refers to an amount suffice at dosages, and for periods of time necessary, to achieve the desired result with respect to suppress the growth of gram-positive bacteria so that it is continuously present for a sufficient period of time to help suppress or inhibit the growth of bacteria. In preferred examples, a sufficient amount of a compound of formula (I) is brought into contact with a bacteria for a certain period of time such that the growth of the bacteria is suppressed for at least 80%, such as 80, 85, 90, 95, or 99%, as compared with that of the un-treated bacteria.

The term "treatment" as used herein are intended to mean obtaining a desired pharmacological and/or physiologic effect, e.g., inhibiting the growth of bacteria, particularly the growth of bacteria having PmrA/PmrB system. The effect may be prophylactic in terms of completely or partially preventing a disease or symptom thereof and/or therapeutic in terms of a partial or complete cure for a disease and/or adverse effect attributable to the disease. "Treatment" as used herein includes preventative (e.g., prophylactic), curative or palliative treatment of a disease in a mammal, particularly human; and includes: (1) preventative (e.g., prophylactic), curative or palliative treatment of a disease or condition (e.g., an infection) from occurring in an individual who may be pre-disposed to the disease but has not yet been diagnosed as having it; (2) inhibiting a disease (e.g., by arresting its development); or (3) relieving a disease (e.g., reducing symptoms associated with the disease). According to specific embodiments of the present disclosure, an effective amount of the compound of formula (I) is administered to a subject suffering from an infection caused by a bacteria, so that the susceptibility of the bacteria (e.g., *Klebsiella pneumoniae*) to certain antibiotic (e.g., Polymyxin B and Colistin) is enhanced, thereby the number of the bacteria in the subject is reduced by at least 80%, such as 80, 85, 90, 95, or 99%, as compared with that of the un-treated subject, and thereby alleviate or ameliorate one or more symptoms associated with the disease, the severity of one or more symptoms associated with the disease and/or the progression of the disease. In preferred embodiments, an effective amount of the compound of formula (I) of the present disclosure is administered to a subject suffering from an infection associated with a disease (e.g., pneumonia, sepsis, cornea infection, skin infection, an infection in the central neuron system, or a toxic shock syndrome), so as to alleviate or ameliorate one or more symptoms associated with the disease, and thereby achieving the purpose of treating the disease.

It should also be noted that if the stereochemistry of a structure or a portion of a structure is not indicated with, for example, bold or dashed lines, the structure or the portion of the structure is to be interpreted as encompassing all stereoisomers of it. Similarly, names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

The singular forms "a", "and", and "the" are used herein to include plural referents unless the context clearly dictates otherwise.

2. Inhibitors of Bacterial Two Component Signal Transduction System (TCS)

The present disclosure is based, at least in part, unexpected discovery that the compound of formula (I), identified from a pharmacophores model of a bacterial response regulator (e.g., PmrA) and DNA complex, are capable of disrupting the formation of the bacterial response regulator and DNA complex, thereby suppressing the growth of the bacteria. More surprisingly, the compound of formula (I) may restore the susceptibility of a multi-drug resistant (MDR) bacteria to an antibiotic that is previously ineffective in killing the MDR bacteria. Thus, the compound of the present disclosure may be used as lead compounds for the development of a medicament for treating a bacterial infectious disease, particularly, the infectious disease caused by MDR bacteria.

The first aspect of the present disclosure thus aims to identify novel TCS inhibitor by screening potential candidate compounds through a pharmacophores model of a bacterial response regulator-DNA complex.

According to preferred embodiments of the present disclosure, a bacterial transcription factor PmrA, which activates genes encoding enzymes that alter the compositions of lipopolysaccharides (LPSs) that eventually increasing bacterial resistance to polymyxin B, is employed to build a PmrA-DNA complex pharmacophores model, i.e., Ch2pharN4 of example 1.1, for screening candidate inhibitors. A total of 10,3000 candidate compounds are respectively fit to the Ch2pharN4 model of example 1.1, and those that aligned well or best fitted with the hot spot residues in the bacterial PmrA-DNA complex are selected as candidate inhibitors, which are further evaluated by microbial inhibition assay to confirm their bioactivity.

According to embodiments of the present disclosure, the identified TCS inhibitor has the structure of formula (I),

A-L-B-L-A    (I)

wherein,

A is a moiety having a negative charge;

L is —(C$_2$H$_5$—O)$_n$—CH$_2$— or a moiety consists of a carbocylyl and a heterocycleyl respectively having 5 to 10 ring atoms and coupling together, in which n is 0 or 1; and B is a 5 to 10-membered carbocyclyl or heterocyclyl; so as to alleviate or ameliorate the symptoms of the bacterial infectious disease.

According to embodiments of the present disclosure, in the formula (I), A is —PO$_4^-$, PO$_3^{2-}$ or In certain embodiments, A is —SO$_3^-$. In other embodiments, A is a —PO$_4^-$.

According to one preferred embodiment of the present disclosure, in the formula (I), A is L is —SO$_3^-$; L is and B is —C$_6$H$_4$—.

According to another preferred embodiment of the present disclosure, in the formula (I), A is —SO$_3^-$; L is —(C$_2$H$_5$—O)$_n$—CH$_2$—, in which n is 1; and B is

According to still another preferred embodiment of the present disclosure, in the formula (I), A is —SO$_3^-$; L is —(C$_2$H$_5$—O)$_n$—CH$_2$—, in which n is 0; and B is

According to embodiments of the present disclosure, the compound of formula (I) is an inhibitor of a bacterial PmrA/PmrB system.

Each compound of formula (I) may be purchased from a commercial source, such as from InterBioScreen Ltd (Moscow, Russia); or may be synthesized in accordance with methods known in the related art.

Shown below are preferred compounds of formula (I) of this disclosure:

E1

E2

E3

3. Uses of TCS Inhibitors

Also within the scope of the present disclosure is a method for treating a subject suffering from a bacterial infectious disease by use of the identified TCS inhibitor. The method includes the step of, administering an effective amount of the compound of formula (I), or a pharmaceutically acceptable salt, hydrate, or solvate thereof, to the subject, so as to alleviate or ameliorate one or more symptoms related to the infectious disease.

According to preferred embodiments of the present disclosure, the compound of formula (I) may be any of the followings,

E1

E2

According to other specific embodiments of the present disclosure, the compound of formula (I) may not be any of, Examples of the bacteria that may cause an infection in the subject include, but are not limited to, *Bacillus anthracis, Bacillus subtilis, Bacillus cereus, Corynebacterium diptheriae, Clostridium tetani, Clostridium botulinum, Clostridium perfringes, Clostridium difficile, Clostridium scindens, Enterococcim Streptococcus viridian, Enterococcus faecalis, Enterococcus foecium, Erysipelothrix rhusiopathiae, Escherichia Coli, Helicobacter pylori, Klebsiella pneumoniae, Listeria monocytogens, Mycobacterium tuberculosis, Propionbacterium acnes, Rhodococcus equi, Staphylococcus agalactiae, Staphylococcus aureus, Staphylococcus epidermidis, Staphylococcus pneumonia, Staphylococcus pyrogens,* or *Staphylococcus saprophyticus.*

According to certain embodiment, the subject has skin abscess, furuncle or skin boil, and thereby resulting the subject prone to bacterial infection. Examples of the bacterial infectious disease include, but are not limited to, pneumonia, sepsis, cornea infection, skin infection, an infection in the central neuron system, and a toxic shock syndrome.

Take pneumonia as an example, the most common bacteria responsible for causing pneumonia is *Klebsiella pneumoniae* or *Streptococcus pneumonia*. Accordingly, certain embodiments of the present disclosure are directed to a method of treating a subject having pneumonia caused by the infection of *Klebsiella pneumoniae* or *Streptococcus pneumonia*. According to certain examples, the *Klebsiella pneumoniae* is a drug-resistant *Klebsiella pneumoniae*, such as polymyxin- or colistin-resistant *Klebsiella pneumoniae*. After administering the compound of formula (I) to the subject, the polymyxin- or colistin-resistant *Klebsiella pneumoniae* would become susceptible to polymyxin or colistin.

According to further embodiments, the present invention is directed to a method for treating s subject suffering from a bacterial infectious disease caused by *Mycobacterium tuberculosis*. In some examples, the *Mycobacterium tuberculosis* is a rifampicin- or isoniazid-resistant *Mycobacterium tuberculosis*. After administering the compound of formula (I) to the subject, the rifamycin- or isoniazid-resistant *Mycobacterium tuberculosis* would become susceptible to rifamycin or isoniazid.

According to still further embodiments, the present invention is directed to a method for treating a subject suffering from a bacterial infectious disease caused by *Helicobacter pylori*. In some examples, the *Helicobacter pylori* is a clarithromycin-resistant *Helicobacter pylori*. After administering the compound of formula (I) to the subject, the clarithromycin-resistant *Helicobacter pylori* would become susceptible to clarithromycin.

In general, the compound of formula (I) is administered to the subject in need thereof in an amount of about 1-100 mg/Kg body weight, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 mg/Kg body weight; preferably about 20-80 mg/Kg body weight, such as 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, and 80 mg/Kg body weight; more preferably about 40-60 mg/Kg body weight, such as 40, 41, 42, 43, 44, 45, 46, 47, 48, 49, 50, 51, 52, 53, 54, 55, 56, 57, 58, 59, and 60 mg/Kg body weight. The amount may be administered in a single dosage or in multiple dosages in a day, such as in 2, 3, or 4 dosages per day. The actual amount of the compound of formula (I) will depend on the specific symptoms of the subject, and the physical conditions of the subject such as age, sex, medical history and etc.; and may be readily determined by the attending physician in accordance with his/her experience.

In some embodiments, the method further includes administering another antibiotic and/or antibacterial agent before, concurrently with, or after the administration of the compound of formula (I). Examples of the antibiotic that may be used with the present compound of formula (I) include, but are not limited to, acumycin, ampicillin, amoxycillin, amphotericins, antimycins, anglomycin, avermectins, azithromycin, boromycin, carbomycins, carbapenem, ceftazidime, cethromycin, chloramphenicol, chalcomycin, ciprofloxacin, concanamycins, cirramycin, clarithromycin, colistin, cycloxacillin, daptomycin, desmethyl azithromycin, desertomycins, dihydropikromycin, dirithromycin, doxycycline, enramycin, erythromycin, flurithromycin, flumequin gentamycin, isoniazid, juvenimicins, kujimycins, lankamycins, lincomycin, litorin, leucomycins, megalomicins, meropenem, methymycin, midecamycins, mycinamicin I, mycinamicin II, mycinamicin III, mycinamicin IV, mycinamicin V, mycinamicin VI, mycinamicin VII, mycinamicin VIII, narbomycin, neoantimycin, neomethymycin, netilmicin, neutromycin, niddamycins, norfioxacin, oleandomycins, oligomycins, ossamycin, oxacillin, oxolinic acid, penicillin, pikromycin, piperacillin, platenomycins, polymyxins, rapamycins, relomycin, rifamycins, rosaramicin, roxithromycin, virginiamycin, spiramycin, sporeamycin, staphococcomycin, streptomycin, sulfamethoxazole, swalpamycin, telithromycin, teicoplanin, timentin, tobramycin, ticarcillin, trimethoprim, tetracyclin, zlocillin, and/or a combination thereof.

4. Pharmaceutical Composition

The present disclosure also encompasses a pharmaceutical composition for treating a bacterial infectious disease, or for suppressing the growth of a bacteria. The pharmaceutical composition comprises an effective amount of the compound of formula (I), its pharmaceutically acceptable salt, hydrate or solvate; and a pharmaceutically acceptable excipient.

The compound of formula (I) of this invention is present at a level of about 0.1% to 99% by weight, based on the total weight of the pharmaceutical composition. In some embodiments, the compound of formula (I) of this invention is present at a level of at least 1% by weight, based on the total weight of the pharmaceutical composition. In certain embodiments, the compound of formula (I) of this invention is present at a level of at least 5% by weight, based on the total weight of the pharmaceutical composition. In still other embodiments, the compound of formula (I) of this invention is present at a level of at least 10% by weight, based on the total weight of the pharmaceutical composition. In still yet other embodiments, the compound of formula (I) of this invention is present at a level of at least 25% by weight, based on the total weight of the pharmaceutical composition.

The pharmaceutical composition is prepared in accordance with acceptable pharmaceutical procedures, such as described in Remington's Pharmaceutical Sciences, 17$^{th}$ edition, ed. Alfonoso R. Gennaro, Mack Publishing Company, Easton, Pa. (1985). Pharmaceutically acceptable excipients are those that are compatible with other ingredients in the formulation and biologically acceptable.

According to some optional embodiments, the pharmaceutical composition further includes, an antibiotic. Examples of suitable antibiotic to be used in the present pharmaceutical composition include, but are not limited to, acumycin, ampicillin, amoxycillin, amphotericins, antimycins, anglomycin, avermectins, azithromycin, boromycin, carbomycins, carbapenem, ceftazidime, cethromycin, chloramphenicol, chalcomycin, ciprofloxacin, concanamycins, cirramycin, clarithromycin, colistin, cycloxacillin, daptomycin, desmethyl azithromycin, desertomycins, dihydropikromycin, dirithromycin, doxycycline, enramycin, erythromycin, flurithromycin, flumequin gentamycin, isoniazid, juvenimicins, kujimycins, lankamycins, lincomycin, litorin, leucomycins, megalomicins, meropenem, methymycin, midecamycins, mycinamicin I, mycinamicin II, mycinamicin III, mycinamicin IV, mycinamicin V, mycinamicin VI, mycinamicin VII, mycinamicin VIII, narbomycin, neoantimycin, neomethymycin, netilmicin, neutromycin, niddamycins, norfioxacin, oleandomycins, oligomycins, ossamycin, oxacillin, oxolinic acid, penicillin, pikromycin, piperacillin, platenomycins, polymyxins, rapamycins, relomycin, rifamycins, rosaramicin, roxithromycin, virginiamycin, spiramycin, sporeamycin, staphococcomycin, streptomycin, sulfamethoxazole, swalpamycin, telithromycin, teicoplanin, timentin, tobramycin, ticarcillin, trimethoprim, tetracyclin, zlocillin, and/or a combination thereof.

The compound of formula (I) of the present invention may be formulated into a single dosage suitable for oral, transmembrane (such as intranasal, sublingual, intravaginal, buccal, and/or endorectal), and/or parenteral administration (e.g., subcutaneous, intravenous, intramuscular, intraperitoneal or bolus injection) Examples of the dosage include, but are not limited to, tablets, caplets, capsules (e.g., soft elastic gelatin capsules), cachets, troches, lozenges dispersions, suppositories, ointments, cataplasms (or poultices) creams, plasters, solutions, patches, aerosols, or gels. The compound of formula (I) of the present invention may be formulated into a liquid pharmaceutical compositions, which are sterile solutions, suspensions (e.g., water solvable or insolvable liquid suspension, oil-in-water emulsion or water-in-oil emulsion) or elixirs that can be administered by, for example, oral ingestion, or intravenous, intramuscular, subcutaneous or intraperitoneal injection.

The compound of the present invention is formulated in accordance with the intended routes for its administration. For example, if the compound of the present invention is intended to be administered by oral ingestion, an enteric coating may be applied on the formulation so as to prevent the compound of the present invention from being degraded in the acidic environment or until it reaches the intestines of the subject. The formulation may further include additional components that help deliver the compound of the present invention to its intended target site. In some examples, the compound of the present invention is enclosed in a liposome to prevent it from enzymatic degradation, and to help transporting the compound of the present disclosure through the circulation system of the subject, and/or across cell membrane to its intended cellular target site.

Further, the least soluble compound of the present invention may be formulated with additional agents, such as a solvating agent, an emulsifying agent and/or a surfactant, into a liquid formulation. Examples of the additional agent include, but are not limited to, cyclodextrin (e.g., α-cyclodextrin and β-cyclodextrin), and non-aqueous solvents, which include but are not limited to, ethanol, isopropanol, ethyl carbonate, ethyl acetate, benzyl alcohol, benzyl benzoate, propyl glycol, 1,3-butyl glycol, dimethyl formamide, dimethyl sulfoxide, biocompatible oils (e.g., cottonseed oil, peanut oil, corn oil, wheat germ oil, castor oil, olive oil, sesame oil, glycerol, tetrahydrogen furan, polyethyl glycol, fatty acid esters of sorbitan, and a combination thereof).

The amount of the compound of the present disclosure in the formulation varies with the route of administration. For example, formulations for acute treatment will contain larger amounts of one or more of the active compounds, as compared to formulations that are for chronic treatment. Similarly, parental formulations will comprise less amounts of one or more of the active compounds, as compared to formulations that are for oral ingestion. Also within the scope of the present disclosure are formulations suitable for other administration routes.

4.1 Formulation for Oral Ingestion

The compound of present disclosure may be formulation into compositions suitable for oral ingestion. Examples of such formulations include, but are not limited to, chewable tablets, tablets, capsules, and syrups, which may be prepared in accordance with procedures described in Remington's Pharmaceutical Sciences (18$^{th}$ ed Mack Publishing, Easton, Pa. (1990)). The oral formulation is prepared by mixing a pre-determined amount of the active compound and one or more pharmaceutically acceptable excipients in accordance with procedures well known in the related art.

Tablets and capsules are two most common forms of oral formulation, which may be either liquid or solid composition form. In general, the tablets and capsules are manufactured by mixing the active components with liquid or milled solid excipients, then press into pre-determined forms. The solid formulation may further include disintegrants, which increase solubility; and lubricants.

4.2 Formulation for Parental Administration

Parental formulations are those suitable for subcutaneous, intravenous (which includes bolus injection), intramuscular, and intraperitoneal injection. To this purpose, sterile injectable or suspension are required so as to prevent the recipients from microorganism infections. Suitable diluents or solvent for manufacturing sterile injectable solution or suspension include, but are not limited to, 1,3-butanediol, mannitol, water, Ringer's solution, and isotonic sodium chloride solution. Fatty acids, such as oleic acid and its glyceride derivatives are also useful for preparing injectables, as are natural pharmaceutically-acceptable oils, such as olive oil or castor oil. These oil solutions or suspensions may also contain alcohol diluent or carboxymethyl cellulose or similar dispersing agents. Other commonly used surfactants such as Tweens or Spans or other similar emulsifying agents or bioavailability enhancers that are commonly used in manufacturing pharmaceutically acceptable dosage forms can also be used for the purpose of formulation.

4.3 Transmembrane Formulation

Transmembrane formulations are those suitable for topical and tansmucosal uses, which include but are not limited to, ophthalmic solutions, sprays, aerosols, creams, lotions, ointments, gels, solutions, suspensions, skin patches and the like. The patches include reservoir type and matrix type skin patches, and may adhere onto the skin for a certain period of time to allow the active component to be adsorbed into the subject's body.

For topical administration, a wide variety of dermatologically acceptable inert excipients well known to the art may be employed. Typical inert excipients may be, for example, water, ethyl alcohol, polyvinyl pyrrolidone, propylene glycol, mineral oil, stearyl alcohol and gel-producing substances. All of the above dosages forms and excipients are well known to the pharmaceutical art. The choice of the dosage form is not critical to the efficacy of the composition described herein.

For transmucosal administration, the pharmaceutical compositions of this invention may also be formulated in a variety of dosage forms for mucosal application, such as buccal and/or sublingual drug dosage units for drug delivery through oral mucosal membranes. A wide variety of biodegradable polymeric excipients may be used that are pharmaceutically acceptable, provide both a suitable degree of adhesion and the desired drug release profile, and are compatible with the active agents to be administered and any other components that may be present in the buccal and/or sublingual drug dosage units. Generally, the polymeric excipient comprises hydrophilic polymers that adhere to the wet surface of the oral mucosa. Examples of polymeric excipients include, but are not limited to, acrylic acid polymers and copolymers; hydrolyzed polyvinylalcohol; polyethylene oxides; polyacrylates; vinyl polymers and copolymers; polyvinylpyrrolidone; dextran; guar gum; pectins; starches; and cellulosic polymers.

The present invention will now be described more specifically with reference to the following embodiments, which are provided for the purpose of demonstration rather than limitation.

EXAMPLES

Materials and Methods

Preparation of Recombinant PmrA/PmrA$_C$ and Oligonucleotides

The DNA fragments which encode full-length PmrA and PmrA$_C$ (residues N121-E223 of PmrA), were cloned into a vector pET-29b(+) (Novagen) with an extra Met residue and a tag (LEHHHHHH, SEQ ID NO: 1) at the N- and C-termini, respectively, in E. coli strain BL21 (DE3). For full-length PmrA, two residues were mutated (W181 to G and 1220 to D) to improve solubility. The mutations were conducted according to the QuickChange site-directed mutagenesis protocol (Stratagene) and confirmed by DNA sequencing. For $^{15}$N-labeled protein samples, cells were grown in H$_2$O containing M9 minimal medium supplemented with $^{15}$NH$_4$Cl and glucose at 37° C., and were disrupted by using an M-110S microfluidizer (Microfluidics). The protein was further purified with nickel-nitrilotri-acetic acid affinity resin (Qiagen, Hilden, Germany). The purity of protein was >95%, examined by coomassie blue-stained sodium dodecyl sulphate (SDS) polyacrylamide gel. Full-length PmrA was activated by BeF3$^-$ (5.3 mM BeCl$_2$, 35 mM NaF and 7 mM MgCl$_2$). The oligonucleotides (5'-ATTTCTTAATATTATCCTAAGCAAG-3', SEQ ID NO: 2) used in fluorescence polarization experiments was from MDBio Inc. (Taiwan) The preparation, purification, and concentration determination of the double-stranded DNA were conducted with the same methods as described previously (Lou, Y C. et al., Nature Communications, 2015, 6, 8838.)

Fluorescence Polarization (FP) Measurements

Compounds, E1-E5, were purchased from InterBioScreen (Moscow, Russia) (E1: STOCK1S-95047; E2: STOCK1N-13224; E3: STOCK1N-16691; E4: STOCK 1 S-43938; E5: STOCK1S-55283), and the purity are over 90% examined by NMR. The oligonucleotides (5'-ATTTCTTAATAT-TATCCTAAGCAAG-3', SEQ ID NO: 2) labeled with 6-car-boxyfluorescein (6-FAM) at the 5'-position, was dissolved in 10 mM sodium phosphate and 15 mM NaCl pH 7.0 for fluorescence polarization experiments. About 10 µl activated PmrA (prepared in 10 mM sodium phosphate and 15 mM NaCl at pH7.0) was first added into the well of ELISA plate. Then, 1 µl of serial diluted inhibitors, E1-E5, (prepared in the sample buffer of activated PmrA) were mixed with the PmrA (final concentration Of 30 µM) to reach the interested concentrations and incubated at 25° C. for 10 mins. Subsequently, 9 µl of 6-FAM-labeled DNA (final concentration of 10 nM) was added into the reaction, incubating at 25° C. for another 10 mins. Reactions were measured 3 times by use of a SpectraMax Paradigm plate reader (Molecular Devices, CA, USA) with excitation wavelength 485 nm and emission wavelength 535 nm. The inhibition % was derived according to the following equation:

$$\text{Inhibition \%} = \frac{\{[(P+D)-(D)] - [(P+I+D)-(D)]\}}{[(P+D)-(D)]} \times 100,$$

in which (D), (P+D), and (P+I+D) are the polarization intensity of DNA alone, PmrA with DNA, and PmrA mixed with inhibitor then incubated with DNA, respectively.

NMR Spectroscopy and Compound Titrations

The preparations of NMR samples were as described previously (Mscielag and Goldschmidt, Expert opinion on investigational drugs 2000, 9, 2351-2369.). Briefly, the activated and inactivated PmrA (0.3 ml, 0.25 mM) were prepared in pH8.0 buffer (20 mM Tris and 100 mM NaCl) with or without BeF$_3^-$ activation. PmrA$_C$ (0.3 ml, 0.25 mM) was prepared in pH8.0 buffer (20 mM Tris and 100 mM NaCl). All the protein solutions were further loaded in Shigemi NMR tubes (Shigemi Inc.). NMR experiments for activated/inactivated PmrA and PmrA$_C$ were conducted at 310 and 298K on Brucker AVANCE 600 or 800 NMR spectrometers (Bruker, Karlsruhe, Germany) equipped with a triple-resonance cryoprobe including a shielded z-gradient. The hetero-nuclear NMR experiments for backbone assignments were performed as described previously in a review article (Garcia-Calderon et al., Journal of Bacteriology 2007, 189, 6635-6644). All the acquired NMR spectra were processed by using NMRPipe (Chen and Groisman, Annual review of microbiology 2013, 67, 83-112) and analyzed with NMRViewJ8.0a.22 (Wosten et al., Molecular microbiology 2006, 60, 39-50). Compound titration experiments were carried out by adding increasing amounts of compound to 0.25 mM $^{15}$N-labeled protein at pH8.0 to reach the interested protein/compound molar ratio and acquiring a serious of 2D-$^1$H—$^{15}$N TROSY-HSQC spectra. The inactivated and activated PmrA titrated with compounds were used to probe the binding site. The titrations of compound toward PmrA$_C$ were employ to determine the dissociation constant ($K_D$). The chemical shift changes were calculated through the equation $\Delta\delta=[(\Delta\delta_{NH})^2+(0.17\times\Delta\delta_N)^2]^{0.5}$, in which $\Delta\delta_{NH}$ and $\Delta\delta_N$ are the chemical shift differences for $^1H_N$ and $^{15}N$, respectively. To determine the dissociation constant ($K_D$), the NMR titration curves of PmrA$_C$ were fitted with the following equation valid for a 1:1 complex in fast exchange: $\Delta v(x)=0.5\times\Delta v_{max}\times\{(x+1+K-[(x+1+K)^2-4x]^{0.5}$, where x is [compound]/[PmrA$_C$], $\Delta v(x)$ is $[(\Delta v_H)^2+(\Delta v_N)^2]^{0.5}$ at molar ratio x, and K corresponds to $K_D$/[PmrA$_C$] (Jo et al., *Antimicrobial agents and chemotherapy* 2011, 55, 2818-2823). The titration curves were fitted and analyzed with the "Titration Analysis" function of NMRViewJ 8.0.a22.

Isothermal Titration Calorimetry (ITC)

The binding affinities of PmrA$_C$ with compound, E1, was estimated by ITC using a MicroCal iTC200 microcalorimeter. The sample of PmrA$_C$ was prepared in reaction buffer (20 mM sodium phosphate, 100 mM NaCl, pH6.0). Compounds were also prepared in reaction buffer (E1=0.4 mM) and titrated into PmrA$_C$ (45 μM) at 25° C. The background heat generated from compound to buffer titration was subtracted, and the corrected heat form the binding reaction of PmrA$_C$ to E1 was used to derive the association constant ($K_a$), the enthalpy of binding ($\Delta H$), the change in Gibbs free energy ($\Delta G$), and the entropy changes ($\Delta S=\Delta H-\Delta G$) at 298K. All the data were analyzed by using Origin ITC Analysis (MicroCal Software, Northampton, Mass., USA).

Bio-Layer Interferometry (BLI)

The BLI kinetics were obtained by using the ForteBio Octet RED96 instrument (ForteBio, Pall Life Sciences). Recombinant PmrA$_C$ carrying C-terminal 6× His tag was immobilized on the HIS1K biosensor in the reaction buffer containing 20 mM sodium phosphate, 100 mM NaCl, pH 6.0 at 25° C. for 180 s prior to kinetic experiment. For the association, the preloading biosensor was exposed to different concentration of E1 (0-37.5 μM) for the period of 300 s. Following the dissociation step, the sensor was subjected to the reaction buffer for 300 s. Kinetic constants, including $K_{on}$ (association constant, $M^{-1}s^{-1}$) and $K_{off}$ (dissociation constant, $s^{-1}$), were obtained by fitting the reaction model 1:1 kinetics to the reference-subtracted data. The equilibrium dissociation ($K_D$) was calculated as the ratio of $K_{off}$ to $K_{on}$. All calculation was determined using Data Analysis 7 software (ForteBio, Pall Life Sciences).

Microbial Viability Assay

Relative survival rate of *Klebsiella pneumoniae* CG43 S3 under antibiotic treatment was determined as previously described (Cheng and Peng, *J. Biomedical Science*, 2010, 17, 60) with some modification. Briefly, the overnight-grown bacterial was subcultured to LB until OD$_{600}$ reached 0.7. Bacterial culture was washed twice with distilled PBS and then 6.7×10$^4$ CFU/ml in LB was prepared. 100 μl of the suspension alone or supplemented with E1 (0, 0.25, 2.5, and 25 μM) was incubated at 37° C. and then placed in each well of a 96-well micro-titer plate, which contained 100 μl PBS or PBS-diluted antibiotics to final concentrations of polymyxin B (0, 0.002, 0.01, and 0.1 μg/ml), colistin (0.1 μg/ml), imipenem (80 m/ml), and kanamycin (64 μg/ml). The plate was incubated at 37° C. for 10, 30, and 60 min with shaking. Subsequently, 100 μl of the suspension was directly plated on LB agar plates and incubated at 37° C. overnight to determine the number of viable bacteria. The relative survival rates were expressed as colony counts divided by the number of the same culture treated with PBS and multiplied by 100. The assays were performed thrice, and the results were expressed as the average±standard derivation from triplicate samples.

Example 1 Receptor-Ligand Pharmacophore Generation and Ligand-Pharmacophore Mapping 1.1 Generation of Pharmacophores Model Ch2pharN4

Figure 1:
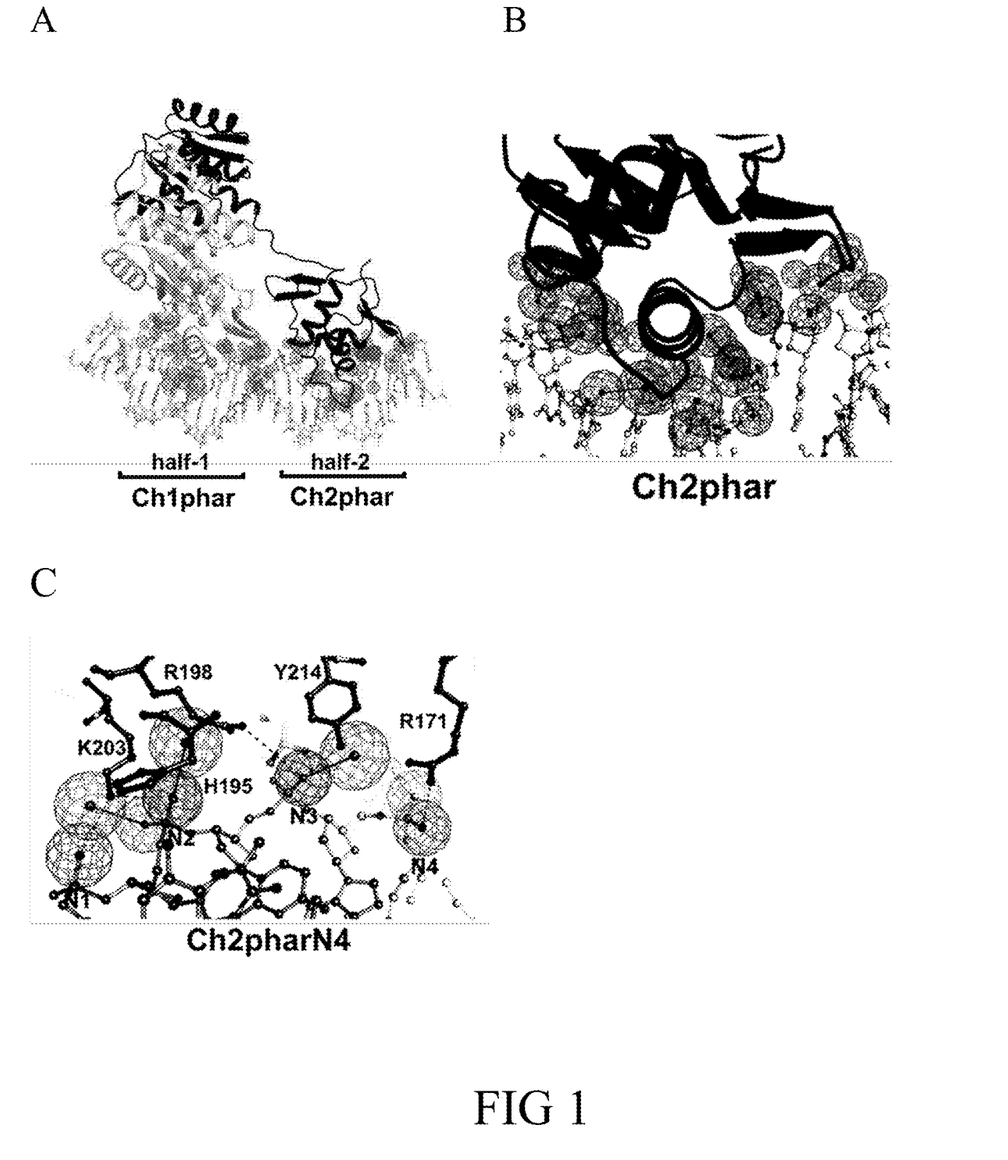

In this example, the receptor-ligand pharmacophore generation module of Discovery Studio 3.5 was employed to build a pharmacophore model for screening candidates of PmrA inhibitor. The complex structure of PmrA-DNA (PDB ID: 4S04) was used to generate the receptor-ligand pharmacophore model. According to previously determined crystal structure of PmrA-DNA complex, two N-terminal receiver domains (RECs) form a twofold symmetrical dimer, and the two DBDs bind to half-1 and half-2 DNA sequences, in a head-to-tail orientation (FIG. 1, panel A). Receptor-ligand pharmacophore generation was performed to comprehensively probe the bioactive features of DNA, functionally essential for targeting PmrA, in which the PmrA structure served as the "Input Receptor," and the DNA structure was utilized as the "Input Ligand." The "Minimum Features" and "Maximum Features" were set to 10 and 30, respectively, and the "Maximum Pharmacophores" were set to 10. The "fast method" was applied for conformation generation with "rigid fitting method." The rest parameters were set as default during the receptor-ligand pharmacophore generation process. Subsequently, pharmacophore feature clusters, Ch1phar and Ch2phar, were rationally generated based on the DBD-half-1 and DBD-half-2 complexes, respectively. Ch1phar contains 1 hydrogen-bond donor, 9 hydrogen-bond acceptors, and 2 negative charged features. Ch2phar consists of 1 hydrogen-bond donor, 7 hydrogen-bond acceptors, 1 positive and 5 negative charged features (FIG. 1, panel B). Notably, the pharmacophore model, Ch2pharN4, constituted of 4 negative charged groups (N1-N4; N2 and N3 could either be the hydrogen-bond acceptors), represents a bioactive scaffold of DNA interacting with residues R171, H195, R198, K203 and Y214 of PmrA (FIG. 1, panel C).

1.2 Screening PmrA Inhibitor Candidates Using Ch2pharN4 of Example 1.1

The built pharmacophores model, Ch2pharN4, was subjected to ligand-pharmacophore mapping. A total of 103,000 molecules were retrieved from natural product databases, including 1,496 compounds from Specs (Specs, The Netherlands), 11,247 compounds from ACD (AnalytiCon Discovery, Postdam, Germany), 144 compounds from ICC (INDOFINE Chemical Company, Inc., Hillsborough, N.J.), 14,084 compounds from PNP (Princeton BioMolecular Research Inc., Princeton, N.J., USA), 1,089 compounds from TCM (Taiwan Chinese medicine) National Research Institute of Chinese Medicine, Ministry of Health and Welfare, Taipei, Taiwan), and 74,940 compounds from the InterBioScreen (IBS) (Moscow, Russia) diversity set. The sketch molecules and prepare ligands modules implemented in Discovery Studio 3.5 (Accelrys Software, Inc., San Diego, Calif., USA) were used to create the molecular structures of all compounds, and hydrogen atoms were present in all the constructed ligands. All the natural products (103,000 compounds) were fit to the built pharmacophore model Ch2pharN4, with the fitting method set to "flexible" and all other parameter were remain as default setting. The visualization of molecular models are achieved by using PyMOL software (http://www.pymol.org).

Total of 5 hits, E1-E5, were observed to better align with the Ch2pharN4 (FIG. 1D) (hierarchy of fitness is E1>E2>E3>E4>E5). Compound, E1, matched all the features of Ch2pharN4; E2 and E3 fitted with N1-N3, while E4 and E5 only matched to N1 and N4. E1-E5 are aromatic sulfonic acid derivatives which contain sulfonic groups at termini probably mimicking the functional phosphate groups of DNA electrostatically interacting with PmrA.

1.3 Characterizing the Functions of the Identified Candidate Compounds E1 to E5 of Example 1.2

Fluorescence polarization (FP) was first employed to access the inhibitory abilities of E1-E5 against the formation of PmrA-DNA complex in accordance with procedures described in the section of "Materials and Methods." Results are depicted in FIG. 1, panels E and F, and Table 1.

It was found that, at 50 µM, E1, E2 and E3 respectively exhibited 70.2±3.2, 55.9±2.7, and 27.41±1.8% inhibitions, while E4 and E5 possessed little or no effect on PmrA binding to DNA (FIG. 1, panel E). Further, E1-E3 exhibited conspicuous dose-dependent inhibitions, with $IC_{50}$ being 10.2±2.6, 42.5±2.9, and 100±2.5 µM, respectively (FIG. 1, panel F; and Table 1). This observation corroborated with the ligand-pharmacophore mapping results of Example 1.2 demonstrating the reliability and precise of Ch2pharN4 in identifying the functional mimetic inhibitors against PmrA-DNA complex formation.

TABLE 1

| $IC_{50}$ of E1-E3 | | | |
|---|---|---|---|
| | E1 | E2 | E3 |
| $IC_{50}$ (µM) | 10.2 ± 2.6 | 42.5 ± 2.9 | 100 ± 2.5 |

Example 2 Characterization of E1

2.1 Identifying the Binding Site of E1

Figure 2:
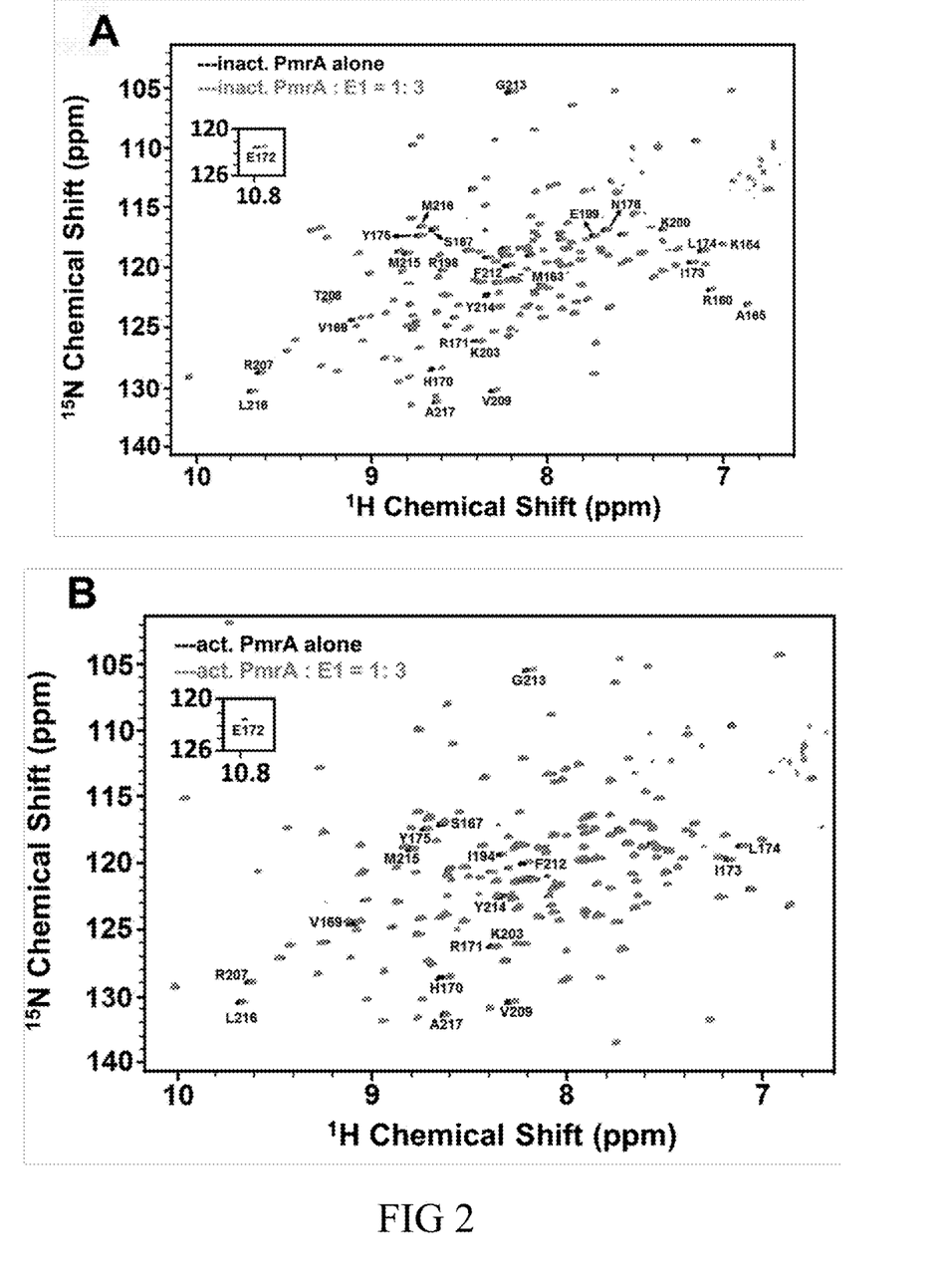

To further identify the binding site of E1, the molecular interactions of E1 toward PmrA were characterized by nuclear magnetic resonance-transverse relaxation optimized spectroscopy (NMR-TROSY) in accordance with procedures described in the section of "Materials and Methods." Upon E1 titration (PmrA: E1=1:3, molar ratio), the TROSY spectra of both inactivated and activated PmrA exhibited obvious chemical shift perturbations (FIG. 2, panels A and B), and the perturbed residues were located at the loop (S167, V169, H170), α7-helix (R171-Y175), and β-hairpin (R207, V209, and F212-A217) of-terminal DBD (FIG. 2C). This revealed that E1 disrupted PmrA binding to DNA by specifically targeting the C-terminal DBD. Furthermore, a series of 2D-$^1$H—$^{15}$N TROSY HSQC spectra were acquired by carrying out titrations of increasing amounts of E1 directly with $^{15}$N-labeled $PmrA_C$ (C-terminal domain of PmrA) in Tris buffer pH8.0 (in phosphate buffer pH6-8, the titrations led to serious amorphous aggregations). The results indicated that residues, S167, V169, R207, V209, R210, Y214, L216 and A217 were perturbed and the positions of their backbone amide resonances changed continuously (FIG. 2, panels D and E). This indicated that E1 binding to occur on the fast-exchange time scale relative to the resonance frequency differences between free and bound forms. Moreover, the titration curves of resonances displaying considerable shift changes were used to determine the dissociation constant ($K_D$) (FIG. 2, panel F). The average $K_D$ value for E1 was determined to be 126±34.6 µM.

The binding affinity of E1 toward $PmrA_C$ (C-terminal domain of PmrA) was further assessed by Isothermal titration calorimetry (ITC) and Bio-layer interferometer (BLI) at the condition described previously (Lou et al., Nature communication 2015, 6, 8838.) (sodium phosphate buffer pH6.0). According to the ITC results, the interaction of E1 with $PmrA_C$ appeared to be an exothermic reaction, with a change in enthalpy (ΔH) of −21.4 kcal/mol, change in entropy (ΔS) of −45.6 kcal/mol per K, and N value of 1.09 (FIG. 2, panel G). Fitting to one set of the site-binding model, the $K_a$ was calculated to be $5.8 \times 10^5$ $M^{-1}$ and the corresponding $K_D$ was 1.7 µM. Also, BLI experiment confirmed the binding of E1 toward $PmrA_C$ and yielded a $K_D$=2.6±0.1 µM, comparable with the result of ITC (FIG. 2, panel H). Additionally, the $K_{on}$ and $K_{off}$ rate were determined to be $(9.494+0.2) \times 10^4$ (1/Ms) and $(2.505+0.1) \times 10^{-1}$ (1/s), respectively, revealing an interaction between E1 and $PmrA_C$ by a fast-on-fast-off binding mechanism, consistence with the NMR titration observation.

2.2 Building the PmrA-E1 Complex

Figure 3:
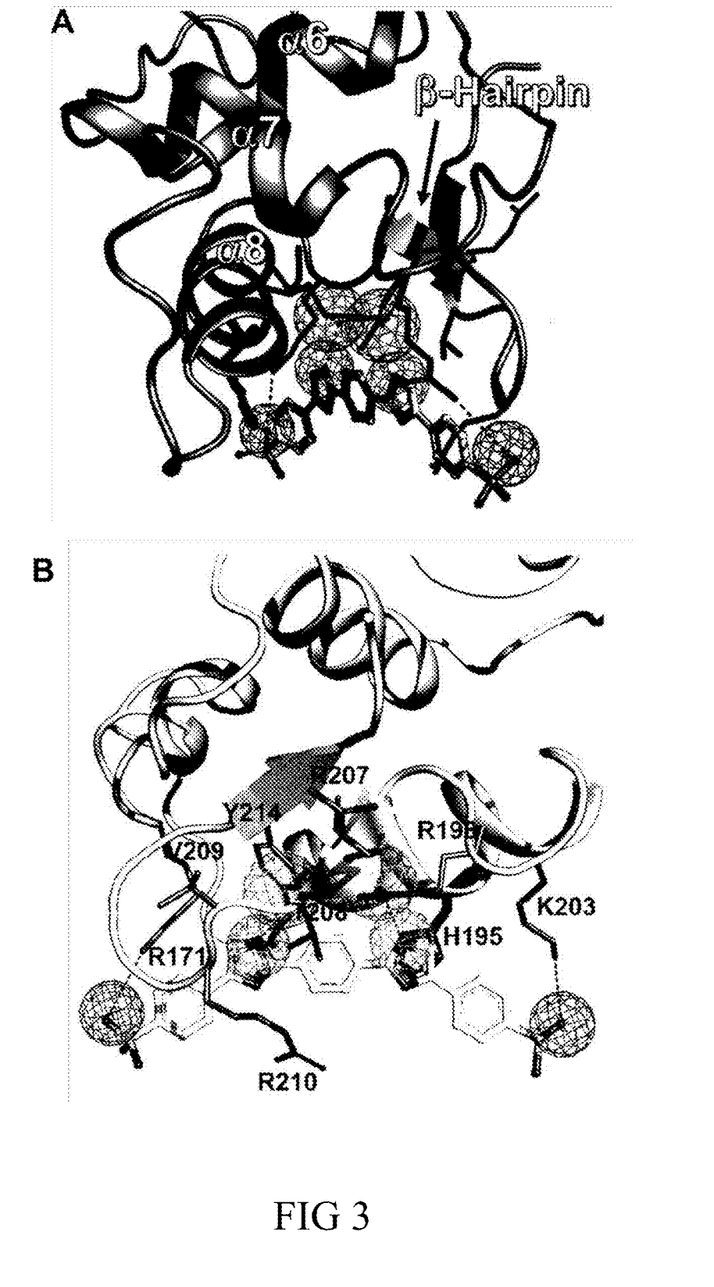
FIG. 3. The complex structure of PmrA-E1 and the microbial viability assay results (A) E1 binds in between α8-helix and C-terminal β-hairpin of DBD and aligned with the pharmacophore scaffold, Ch2pharN4. (B) The residues of PmrA interact with E1 are shown in sticks (magenta) and labeled in black. (C) The 2D illustration of detailed interactions of E1 with PmrA. (D) The effects of E1 on polymyxin B dose-dependent inhibition of KP.

To gain more insights into the atomic interactions between E1 and PmrA, we performed molecular modeling to construct the structure of the complex. The residues of the activated PmrA that were perturbed upon E1 titration (according to the NMR results) were defined as constituting the binding site in protein-ligand flexible docking. The side chains of the binding site residues were set to be flexible so they could access distinct rotamers during docking analysis. Finally, the lower energy model with E1 fulfilled all features of Ch2pharN4 was selected as the complex structure of PmrA-E1. The built structure revealed that E1 bound in-between of α8-helix and β-hairpin of C-terminal DBD (FIG. 3, panels A and B). The detailed molecular interactions of E1 with PmrA was depicted in FIG. 3, panel C. In this binding model, the terminal sulfonic groups of E1, fitting to N1 and N4 of Ch2pharN4, interacted with residues R171 and K203 through charge-charge interactions. The tertiary amine of the two oxazole rings, matching with N2 and N3 of Ch2pharN4, formed hydrogen-bonds with side chains of R198 and Y214. Additionally, the εNH group of R210 and the side chain amide of K203 formed cation-pi interactions with the left oxazole ring and right terminal benzene ring, respectively. Also, the carboxyl group of E191 formed an anion-pi interaction with the left oxazole ring. The methyl group of T208 and the imidazole ring of H195 made contacts with the middle benzene and right oxazole rings through hydrophobic and pi-pi interactions, respectively. On the other hands, loop residues S167-H170, α7-helix residues E172-Y175, and C-terminal residues M215-A217 showed no direct contacts with E1 yet were disturbed in the TROSY spectra, suggesting that the binding of E1 may have induced the occurrence of minor conformational changes in these regions.

2.3 E1 Enhances Microbial Susceptibility to Polymyxin B

To access the effect of E1 on the susceptibility of *Klebsiella pneumoniae* (KP) to Polymyxin B, the microbial viability assay was performed. The results appeared to show that bactericidal ability of Polymyxin B (at distinct concentrations) against KP was enhanced in the presence of E1 (2.5 µM) (FIG. 3, panel D). This result indicated that E1 may restore the susceptibility of KP to Polymyxin B. Additionally, this adjuvant activity of E1 to colistin (polymyxin E) on killing KP was also observed (data not shown). Moreover, the BLAST search against pdbaa database showed that the C-terminal DBD of KP PmrA shares structure and sequence similarity with other response regulators (RRs) of pathogenic bacteria. Notably, the conserved region covered the residues interacting with E1, particularly at the positions of R171, R198, K203, and Y214 of PmrA (data not shown). This observation revealed that E1 could target the RRs of the pathogenic bacteria, such as *Mycobacterium tuberculosis* (MtrA) and *Helicobacter pylori* (ArsR and hp1043), exerting broad-spectrum bactericidal activities.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of inhibiting bacterial growth in a subject, comprising administering to the subject, an effective amount of a compound of formula (I), or a pharmaceutically acceptable salt, hydrate or solvate thereof,

A-L-B-L-A    (I)

wherein,
A is a moiety having a negative charge, which is selected from the group consisting of $PO_4^-$, $PO_3^{2-}$, and $SO_3^-$;
L is and
B is —$C_6H_4$—;
an antibiotic selected from the group consisting of colistin, polymyxins, rapamycins, and a combination thereof, and
the bacteria is any of *Escherichia Coli*, *Klebsiella pneumoniae*, or *Staphylococcus aureus*.

2. The method of claim 1, wherein A is —$SO_3^-$.

3. The method of claim 1, wherein the compound of formula (I) is an inhibitor of a bacterial PmrA/PmrB system.

4. The method of claim 1, wherein the bacteria is multi-drug resistant (MDR) bacteria.

5. The method of claim 4, wherein the bacteria is polymyxin- or colistin-resistant *Klebsiella pneumoniae*.

* * * * *